United States Patent [19]

Crossley

[11] Patent Number: 4,873,237
[45] Date of Patent: Oct. 10, 1989

[54] 2,3-DIHYDRO- THIAZOLO- AND THIAZINO- BENZIMIDAZOLES AS ANTI-HYPER SECRETION AGENTS

[75] Inventor: Roger Crossley, Reading, England

[73] Assignee: John Wyeth & Brother Limited, Maidenhead, England

[21] Appl. No.: 866,636

[22] Filed: May 22, 1986

Related U.S. Application Data

[63] Continuation-in-part of Ser. No. 619,870, Jun. 12, 1984, abandoned.

[30] Foreign Application Priority Data

Jun. 18, 1983 [GB]  United Kingdom ................. 8316645

[51] Int. Cl.$^4$ ..................... A61K 31/54; C07D 513/04
[52] U.S. Cl. ............................... 514/222.8; 544/375; 544/132; 544/34; 548/151; 548/324; 514/322; 514/398; 514/366; 514/233.2; 514/231.8; 514/232.2; 514/232.5; 514/255; 514/316; 514/318; 514/314; 514/338; 546/271; 546/144; 546/167
[58] Field of Search ................... 544/375, 132, 34; 548/305, 151, 324; 514/322, 255, 398, 366; 546/271, 144, 167

[56] References Cited

U.S. PATENT DOCUMENTS 4,214,089  7/1980  Fenichel et al. ................... 548/151

FOREIGN PATENT DOCUMENTS 56-18989  2/1981  Japan ................................. 544/32
5583710   1/1982  Japan ................................ 548/305

OTHER PUBLICATIONS

Chem. Abstracts, vol. 95 (No. 9) Abst. No. 95: 80996d Aug. 31, 1981.

Primary Examiner—Richard A. Schwartz
Assistant Examiner—Robert C. Whittenbaugh
Attorney, Agent, or Firm—George Tarnowski

[57] ABSTRACT

The invention relates to a method of treatment of ulcers or hypersecretion in a mammal which comprises administering a compound of formula

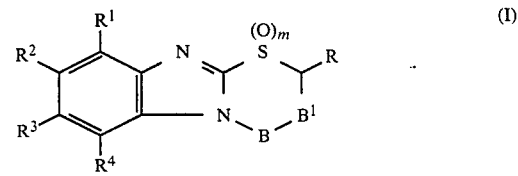

or a pharmaceutically acceptable salt thereof wherein —B—B$^1$— represents a chain of formula $$-(CHR^5)_n-CHR^6- \quad \text{(Ia)}$$

R represents an optionally substituted aryl or heteroaryl radical,

R$^1$, R$^2$, R$^3$ and R$^4$ independently represent hydrogen, or a defined substituent or any adjacent pair of R$^1$, R$^2$, R$^3$ and R$^4$ together with the carbon atoms to which they are attached complete a five or six membered saturated or unsaturated carbocyclic or heterocyclic ring, said ring being optionally substituted by a defined substituent and said heterocyclic ring having at least one heteroatom selected from oxygen, nitrogen and sulphur;

R$^5$ and R$^6$ independently represent hydrogen or lower alkyl; n and m independently represent 0 or 1, the term "heteroaryl" means a monovalent aromatic heterocyclic group in which the ring heteroatom or atoms is/are selected from oxygen, nitrogen and sulphur. Novel Compositions and compounds of formula I are also disclosed.

22 Claims, No Drawings

2,3-DIHYDRO- THIAZOLO- AND THIAZINO-BENZIMIDAZOLES AS ANTI-HYPER SECRETION AGENTS

This invention relates to a method for treating ulcers or hypersecretion with heterocyclic compounds more particularly benzimidazoles, to novel compositions comprising benzimidazoles and to the novel compounds themselves and their preparation and is a continuation-in-part of co-pending application Ser. No. 619,870 filed 12th Jun. 1984, now abandoned.

2,3-Dihydrothiazino-benzimidazoles having hypotensive activity are disclosed in Japanese Kokai 8118989 (Chemical Abstracts 95:80996d). Krasovskii OM in Farm. Zh (Kiev) 1979, (4) 33036 disclosed naphth-[1′,2′:4,5]imidazo[2,1-b]-thiazoles in a study (no data) of compounds with antibacterial and antifungal activities. Thiazolo[3,2-a]benzimidazoles are described in the following Chemical Abstracts references: 72:43565s; 76:52165w; 81:151141v; 73:109740z; 71:22067v; 71:13065r; 76:153678w; 76:153679x and 92:41839y; but no pharmaceutical activity is ascribed to the compounds.

A series of 2,3-dihydro-thiazolo- and thiazinobenzimidazoles has been found which possesses pharmaceutical activity, in particular antiulcer activity and/or antisecretory activity and hence is useful in the treatment of ulcers or gastric hypersecretion. In particular the compounds are useful in the treatment of peptic ulcer disease. The compounds are also useful as intermediates to other compounds in the series.

Accordingly in one aspect this invention provides a method of treating ulcers or hypersecretion in a mammal which comprises administering to said mammal in need of such treatment an effective amount of a compound of formula:

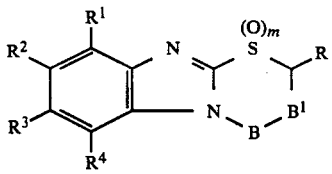

or a pharmaceutically acceptable salt thereof wherein —B—B$^1$— represents a chain of formula

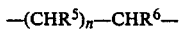 (Ia)

R represents an aryl or heteroaryl radical each optionally substituted by one or more substituents the same or different selected from lower alkylthio, lower alkyl, lower alkoxy, halogen, alkanoyloxy of 2 to 7 carbon atoms, lower alkoxycarbonyl, halolower alkyl, hydroxy, cyano, amino, mono- or diloweralkyl amino, lower alkanoylamino, carboxy, carboxyloweralkyl, hydroxyloweralkyl, carbamoyl, carbamoyloxy, lower alkyl- or aryl-carbonyl, (loweralkoxy)lower alkoxy, 1-piperidinyl, 4-morpholinyl, 4-loweralkylpiperazinyl, 1-pyrrolidinyl, OR$^8$, SR$^8$, phenyl, and phenyl substituted by one or more substituents as hereinbefore defined excepting phenyl; (where R$^8$ is C$_2$-C$_6$ alkenyl, C$_3$-C$_{10}$ cycloalkyl, aryl, aralkyl or aryl or aralkyl each carrying from 1 to 3 substituents on the aryl selected from lower alkyl, halogen, nitro, haloloweralkyl, hydroxy and lower alkoxy);

R$^1$, R$^2$, R$^3$ and R$^4$ independently represent hydrogen, or a substituent as mentioned above in connection with the group R; or any adjacent pair of R$^1$, R$^2$, R$^3$ and R$^4$ together with the carbon atoms to which they are attached complete a five or six membered saturated or unsaturated carbocyclic or heterocyclic ring, said ring being optionally substituted by a substituent as defined above in connection with the group R, said heterocyclic ring having at least one heteroatom selected from oxygen, nitrogen and sulphur;

R$^5$ and R$^6$ independently represent hydrogen or lower alkyl; n and m independently represent 0 or 1, the term "heteroaryl" means a monovalent aromatic heterocyclic group in which the ring heteroatom or atoms is/are selected from oxygen, nitrogen and sulphur; the term 'lower' means a group containing 1 to 6 carbon atoms.

In a second aspect this invention provides novel compounds of formula I as shown hereinabove or salts thereof, wherein R, R$^1$, R$^2$, R$^3$, R$^4$, m and —B—B$^1$— have the meanings given above with the provisos:

(i) when n is 1 and m is 0 then R is optionally substituted heteroaryl, (ii) when n is 0, R$^1$ and R$^2$ together with the carbon atoms to which they are attached represent a 6 membered unsaturated carbocyclic ring and R is phenyl or p-nitrophenyl then m is 1.

In a third aspect this invention provides pharmaceutical compositions comprising a compound of formula I as shown hereinbefore or a pharmaceutically acceptable salt thereof wherein R, R$^1$, R$^2$, R$^3$, R$^4$, m and —B—B$^1$— have the meanings given above with the proviso that when n is 1 and m is 0 then R is optionally substituted heteroaryl.

Examples of any one of R$^{1-4}$ when substituents are methyl, ethyl, propyl, butyl, isopropyl, methoxy, ethoxy, propoxy, isopropoxy, butoxy, chlorine, bromine, fluorine, acetoxy, propionyloxy, butryloxy, methoxycarbonyl, ethoxycarbonyl, propoxycarbonyl, trifluoromethyl, hydroxy, cyano, amino, methylamino, dimethylamino, ethylamino, acetylamino, carboxy, carboxymethyl, hydroxymethyl, hydroxyethyl, carbamoyl, carbamoyloxy, acetyl, benzoyl or phenyl.

The group R is exemplified by (1) aryl radicals such as phenyl or naphthyl which can be substituted by one or more groups as listed above for any one of R$^{1-4}$, and (2) heteroaryl radicals especially those having one or more heteroatoms selected from oxygen, nitrogen and sulphur, such as pyridyl (e.g. pyrid-2-yl, pyrid-3-yl), thienyl (e.g. thien-2-yl) furyl (e.g. fur-2-yl), thiazolyl e.g. thiazol-2-yl), or bicyclic groups such as quinolyl, isoquinolyl or indolyl, which groups can be substituted by one or more groups as listed above for any one of R$^{1-4}$. Examples of substituents for R also include (lower alkoxy)- lower alkoxy (e.g. methoxymethoxy, methoxy- and ethoxyethoxy), phenyl, halophenyl, loweralkylphenyl, loweralkoxyphenyl, methylthio, ethylthio, propylthio, butylthio, pentylthio, isopropylthio, t-butylthio, and groups of formula OR$^8$ or SR$^8$ where R$^8$ is vinyl; 1-propenyl; 3-butenyl; cyclopropyl; cyclobutyl; cyclopentyl; cyclohexyl; cycloheptyl; cyclooctyl; cyclononyl; cyclodecyl; 2-methylcyclopropyl; 2,2-dimethylcyclopropyl; 2-methylcyclobutyl; 2-methylcyclopentyl, 2-methylcyclohexyl; phenyl; o-, m- or p-tolyl; o-, m- or p-ethylphenyl; 2,3-, 3,4-, 3,5- or 2,5-dimethylphenyl; 2,3,5-, or 3,4,5-triethylphenyl; 2-, 3- or 4-chlorophenyl; 2-, 3- or 4-fluorophenyl; 2,3-, 3,4- or 2,4-dichlorophenyl; o-, m- or p- methoxyphenyl; 2,3-, 3,4-, or 2,4-dimethoxyphenyl; 2-chloro-3-methylphenyl; 2-chloro-4 -methoxyphenyl; benzyl and 2-chlorobenzyl.

When any adjacent pair of $R^1$, $R^2$, $R^3$ and $R^4$ complete a fused ring examples of the additional rings are benzoand pyrido-fused rings. For example when $R^2$ and $R^3$ form a benzo fused ring the compound of formula I has the general formula

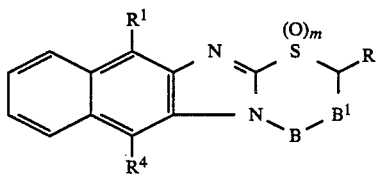

Examples of $R^5$ and $R^6$ when lower alkyl are methyl, ethyl, propyl.

In the compounds of formula I preferred value for n is 0.

Preferably R represents a phenyl or pyridyl group e.g. pyrid-2- or 3-yl which may be substituted e.g. by up to 4 substituents the same or different as hereinbefore described, especially lower alkyl, lower alkoxy, lower alkylthio, halogen, phenyl, halophenyl, lower alkylphenyl or lower alkoxyphenyl. Preferably m is 1. Preferably either or both $R^2$ and $R^3$ represent substituents selected from lower alkyl (e.g. methyl or ethyl) lower alkoxycarbonyl, (e.g. methoxycarbonyl); halogen (e.g. chlorine or bromine) or $R^2$ and $R^3$ are both hydrogen.

A preferred group of compounds for use in this invention has the general formula Id

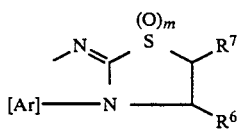

and salts thereof, wherein [Ar] represents

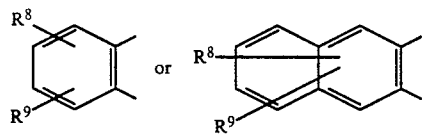

$R^7$ is a phenyl or a pyridyl group either of which may be substituted preferably by up to 3 substituents the same or different as hereinbefore defined, most preferably selected from lower alkyl, lower alkylthio lower alkoxy and halogen; $R^8$ and $R^9$ independently represent hydrogen or a substituent selected from lower alkyl, lower alkoxy, halogen, cyano, carboxy, loweralkoxycarbonyl, alkanoyloxy of 2 to 7 carbon atoms, carbamoyl, hydroxy, hydroxyalkyl, haloloweralkyl, amino; $R^6$ is as hereinbefore defined and m is 0 or 1.

Preferred compounds of the invention include 2,3-dihydro-2-(2-pyridyl)thiazolo[3,2-a]benzimidazole-1-oxide; 6,7-dichloro-2,3-dihydro-2-(2-methylpyrid-5-yl)thiazolo-[3,2-a]benzimidazole; 2,3-dihydro-6,7-dimethyl-2-(2-pyridyl)-thiazolo[3,2-a]-benzimidazole-1-oxide; 6 or 7-chloro-2,3-dihydro-2-(2-pyridyl)-thiazolo[3,2-a]-benzimidazole-1-oxide;

Examples of acid addition salts are those formed from inorganic and organic acids, in particular pharmaceutically acceptable acid addition salts such as the hydrochloride, hydrobromide, hydroiodide, sulphate, nitrate, phosphate, sulphonate (such as the methanesulphonate and p-toluenesulphonate) acetate, maleate, citrate, fumarate, tartrate, malonate and formate. The salts also include quaternary ammonium salts such as those formed from alkyl or aralkyl halides.

The compounds of formula I possess antiulcer and/or anti-secretory activity as measured by standard test procedures and accordingly are useful for the treatment of ulcers or hypersecretion in mammals.

Anti-ulcer activity was determined by the stressinduced erosion test of Senay and Levine, Proc. Soc. Exp. Biol. Med., 124, 1221-3 (1967). The procedure used was as follows.

Male rats, weighing between 80 and 120 gms. were fasted overnight with water ad lib. The rats were then divided into groups of six and dosed orally with the test drug in the form of a solution or with the vehicle alone, 0.5% carboxymethylcellulose, in a volume of 10ml/kg.

After 30 minutes the rats were inserted into aluminium restraining tubes measuring 1⅜ inches in diameter by 5 inches and placed in the cold (4±1° C.) for 3 hours. Immediately after cold exposure the rats were killed with intracranial alcohol and their stomachs excised and opened along the greater curvature. Each stomach was washed gently free of contents with warm tap water and pinned out on a board. The condition of the gastric mucosa was then scored from 0 to 6 on the following scale:

Ulcers

| 0-6 | 0 | = No ulcers |
|---|---|---|
|  | 1 | = Pin point haemorrhagic site |
|  | 2 } | = Several discrete pin point haemorrhagic sites |
|  | 3 } |  |
|  | 4 |  |
|  | 5 } | = Large eroded sites with haemorrhage |
|  | 6 } |  |

The maximum possible score for each animal was 6 and for the group 36. Decrease in ulcer formation was calculated as a percentage of the control score, i.e.

$$\text{Percentage Inhibition} = \frac{\text{Mean Control group score} - \text{Mean Test group score} \times 100}{\text{Mean Control group score}}$$

The statistical significance of the effect is assessed by Student's t-test. Experience has shown that +45% inhibition may be taken as a threshold value below which compounds can be regarded as inactive or not sufficiently active to be considered further.

In the above mentioned test the following representative compounds of formula I were particularly active giving results as shown:

|  | Dose (mg/kg) | Inhibition |
|---|---|---|
| 2,3-dihydro-2-(2-pyridyl)-thiazolo[3,2-a]benzimidazole | 100 | 75% |
|  | 30 | 86% |
| 2,3-dihydro-6,7-dimethyl-2-(2-pyridyl)thiazolo[3,2-a]-benzimidazole | 100 | 82% |
| 2,3-dihydro-2-phenylthiazolo-[3,2-a]benzimidazole | 100 | 74% |

Antisecretory activity was demonstrated by the test of H. Shay, D. Sun and H. Gruenstein, Gastroenterology. 1954, 26, 903–13 as exemplified by Beattie et al, J.Med. Chem. 20, 714 (1977). In this test the following representative compounds of formula I were particularly active:
(a) 2,3-dihydro-2-(2-pyridyl)thiazolo[3,2-a]benzimidazole and its 1-oxide.
(b) 2,3-dihydro-6 or 7-methyl-2-(2-pyridyl)thiazolo[3,2-a]-benzimidazole.
(c) 2,3-dihydro-6,7-dimethyl-2-(2-pyridyl)thiazolo[3,2-a]-benzimidazole and its 1-oxide.
(d) 2,3-dihydro-6 or 7-methyl-2-(2-pyridyl)thiazolo[3,2-a]-benzimidazole-1-oxide.
(e) 2,3-dihydro-6- or 7-chloro-2-(2-pyridyl)thiazolo[3,2-a]-benzimidazole-1-oxide.

Compounds of formula I were also tested for antisecretory activity by their ability to inhibit the highly specific proton transporting enzyme $H^+/K^+$ ATPase.

Potential $H^+/K^+$ ATPase inhibitors were evaluated by a technique involving the measurement of aminopyrine accumulation in rabbit isolated gastric glands. Aminopyrine accumulates in acid-secreting cells; therefore, uptake of aminopyrine is increased by secretagogues and an inhibitor of acid secretion will reduce the response to one or more secretagogues depending upon its site of action. Compounds which reduce the response to dibutyryl cyclic adenosine monophosphate (DBcAMP) stimulation are assumed to have an intracellular site of action; and those which reduce the response to both DBcAMP and high potassium ion concentration ($K^+$) are thought to have an intracellular site of action at the secretory surface of the parietal cell, involving the highly specific proton-transporting enzyme, $H^+/K^+$ ATPase.

The following test procedure is used:

Rabbit gastric glands are isolated from gastric mucosa from the corpus region of the stomach by a method based on one described by Berglindh T., Obrink K. J., Acta Physiol. Scand. 96, 150-159 (1976). Measurement of aminopyrine uptake is carried out using a procedure based on the method described by Berglindh T., Hellander H. F., Obrink K. J. (ibid.97, 401-414, 1976).

Compounds are tested at a concentration of $10^{-4}M$ initially, and in some cases at lower concentrations, for their ability to inhibit $^{14}C$-aminopyrine uptake in gastric glands, stimulated by DBcAMP and high $K^+$ respectively. Results are expressed as the % inhibition of the maximum response to the secretagogue induced by the test compound. An inhibitor of $H^+/K^+$ ATPase would be expected to reduce the response to both secretagogues.

In the above test the following compounds of formula I were particularly active giving the results shown:

| Compound | % Inhibition to stimulation by: | |
|---|---|---|
| | DBcAMP | $K^+$ |
| 2,3-dihydro-2-(2-pyridyl)-thiazolo[3,2-a]benzimidazole-1-oxide | 74% at $10^{-4}$ M<br>73% at $10^{-5}$ M | 91% at $10^{-4}$ M<br>26% at $10^{-5}$ M |
| 6,7-dichloro-2,3-dihydro-2-(6-methylpyrid-3-yl)-thiazolo[3,2-a]benzimidazole | 90% at $10^{-4}$ M | 187% at $10^{-4}$ M |
| 6,7-dichloro-2,3-dihydro-2-(2-pyridyl)-thiazolo-[3,2-a]-benzimidazole | 50.5% at $10^{-4}$ M | 74% at $10^{-4}$ M |
| 2,3-dihydro-6,7-dimethyl-2-(2-pyridyl)thiazolo[3,2-a]-benzimidazole-1-oxide | 30% at $10^{-4}$ M | 209% at $10^{-4}$ M |

This invention also provides processes for preparing the novel compounds of formula I. In general the compounds may be prepared by processes which are known or are analogous to known processes - see literature references hereinbefore disclosed.

A first process for preparing compounds of formula I comprises cyclising a compound of formula

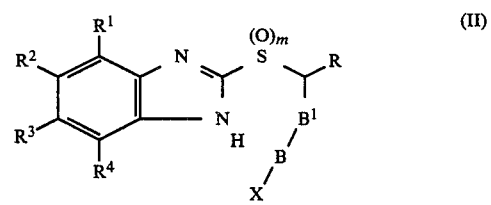

wherein $—B—B^1—$, n, m, R, $R^1$, $R^2$, $R^3$, $R^4$, $R^5$ and $R^6$ are as defined above, and X is a leaving group such as halogen or an aryl-, alkyl- or aralkyl-sulphonyloxy group that couples B to nitrogen. This cyclisation is conveniently carried out in a suitable solvent if desired under basic conditions (e.g. triethylamine, potassium carbonate) and with heating if required.

Compound of formula II can in general be prepared by reacting an appropriate 2-chlorobenzimidazole with a compound of formula

wherein R, $—B—B^1—$ and X are as hereinbefore defined and if desired oxidising the product, e.g. using a peroxyorganic acid such as peroxybenzoic acids.

Using this reaction it is possible to go directly to the corresponding compounds of formula I without isolating the intermediates of formula II.

In a preferred process for preparing the compounds of formula I the compounds of formula II wherein m is O are prepared and cyclised without isolation in a single step process by reacting an appropriate 2-mercaptobenzimidazole of formula

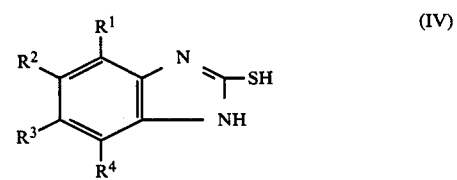

wherein $R^1$, $R^2$, $R^3$ and $R^4$ are as defined above with a compound of formula

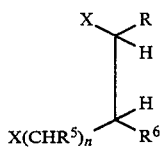

wherein R, $R^5$ $R^6$ and n are as hereinbefore defined, the X groups being the same or different halogens. This reaction is conveniently carried out by heating in a suitable solvent, e.g. dimethylformamide, if desired in the presence of base.

It should be noted that due to tautomerism certain ring substituted 2-mercaptobenzimidazole starting materials are mixtures and hence mixtures of final products are obtained. For example 2-mercapto-5-methylbenzimidazole is tautomeric with 2-mercapto-6-methylbenzimidazole and the final product will be a mixture of compounds where $R^2$ or $R^3$ is methyl.

A further process for preparing the compounds of formula I wherein m is O comprises cyclising a compound of formula

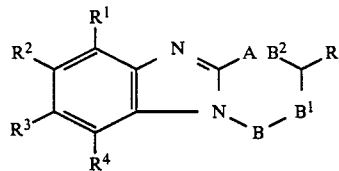

wherein —B—$B^1$—, n, R, $R^1$, $R^2$, $R^3$, $R^4$, $R^5$ and $R^6$ are as hereinbefore defined and one of A and $B^2$ is -SH, the other is a leaving group providing that when A is SH then $B^2$ may also represent OH.

When A or $B^2$ is a leaving group the cyclisation is generally carried out by heating if desired in the presence of base, e.g. triethylamine, $K_2CO_3$, NaOH, etc. When $B^2$ is OH the cyclisation may be carried out in the presence of a strong acid, e.g. HCl or polyphosphoric acid.

Compounds of formula VI wherein A is SH and $B^2$ is OH may be prepared by
(a) reacting an appropriate 2-chlorobenzimidazole with a compound of formula

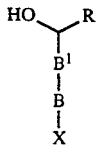

wherein —B—$B^1$—, X, R, $R^5$ and $R^6$ are as hereinbefore defined to give a compound of formula VIII

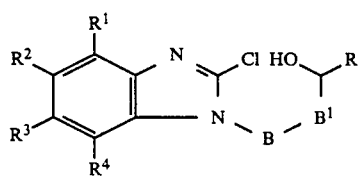

wherein —B—$B^1$—, $R^1$, $R^2$, $R^3$, $R^4$, $R^5$ and $R^6$ are as hereinbefore defined and
(b) reacting the compound of formula VIII with thiourea and to give a 2-isothiouronium compound and treating this with an alkali metal hydroxide or ammonium hydroxide under mild conditions, e.g. reacting at room temperature or without heating.

Compounds of formula VI wherein A is SH and $B^2$ is a leaving group and —B—$B^1$— has formula I a may be prepared from the corresponding compounds of formula VI wherein $B^2$ is OH by known methods e.g. halogenation, sulphonylation to convert OH to a leaving group.

Compounds of formula VI wherein A is a leaving group such as halogen and $B^2$ is SH may be prepared by building up the molecule from appropriate starting materials wherein the -SH is protected by a thiol protecting group and removing the protecting group as the final step.

Compounds of formula I wherein m is 0, —B—$B^1$— has formula Ia and either n is 1 and $R^5$ is hydrogen or n is 0 and $R^6$ is hydrogen may also be prepared by a process which comprises reducing a compound of formula

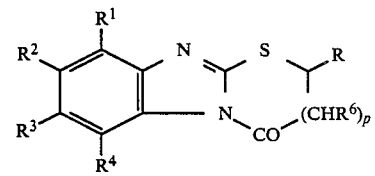

wherein R, $R^1$, $R^2$, $R^3$, $R^4$ and $R^6$ are as hereinbefore defined and p is 0 or 1.

This reduction may be carried out using a metal hydride, e.g. lithium aluminium hydride.

The compounds of formula IX may be prepared by cyclising a corresponding compound of formula X

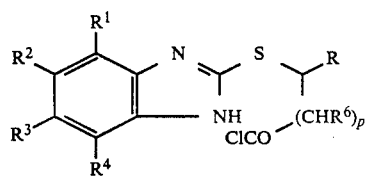

wherein p, R, $R^1$, $R^2$, $R^3$, $R^4$ and $R^6$ are as defined above.

Compounds of formula X may be prepared by reacting the appropriate 2-mercaptobenzimidazole with a haloacid of formula $RCHBr(CHR^6)_pCOOH$ (R, $R^6$ and p as defined herein) and converting the acid to the acid chloride.

In yet a further process the compounds of formula I wherein m is 0 may be prepared by reacting a compound of formula

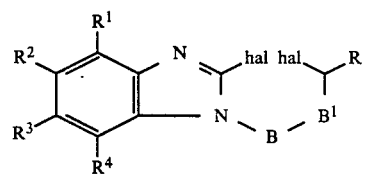

wherein —B—$B^1$—, hal, n, R, $R^1$, $R^2$, $R^3$, $R^4$, $R^5$ and $R^6$ are as hereinbefore defined with
(i) an alkali metal sulphide or hydrosulphide,
(ii) ammonium sulphide or polysulphide or (iii) H$_2$S in the presence of a tertiary amine.

Compounds of formula I wherein m is 0 and 1 may be interconverted. For example when m is 0 the compounds may be oxidised to the corresponding oxides of formula I wherein m is 1 by treatment with suitable oxidising agents e.g. hydrogen peroxide, sodium periodate, peroxy acids such as peroxybenzoic acids and peroxyalkanoic acids. When m is 1 the compound of formula I may be reduced to the corresponding compound where m is 0 using a reducing agent such as a metal or boron hydride, eg. BHCl$_2$. Accordingly compounds of formula I are intermediates for other compounds of formula I.

The compounds of formula I possess one or more asymmetric centres and hence optical isomers and mixtures thereof are possible. All such isomers and mixtures thereof are included within the scope of this invention. Where any reaction process produces mixtures of such isomers standard resolution techniques may be applied to separate a specific isomer.

In any of the aforementioned reactions compounds of formula I may be isolated in free base form or as acid addition salts as desired. Quaternary ammonium salts may be prepared by reaction with an appropriate halide.

Processes as described hereinabove which prepare novel compounds of formula I are within the scope of this invention.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form.

The anti-ulcer compositions of the invention will be adminsitered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British specification No. 1,284,394.

In another aspect the invention provides as an anti-ulcer agent a compound of formula I or a pharmaceutically acceptable salt thereof as defined above.

The following examples illustrate the invention:

EXAMPLE 1

2,3-Dihydro-2-(2-pyridyl)thiazolo[3,2-a]benzimidazole

To 2-(1-,2-dibromoethyl)pyridine hydrobromide (10g) dissolved in dimethyl formamide (250 ml) was added 2-mercaptobenzimidazole (7 g) and the mixture was stirred at 60° C. for 36 hours. The solvent was removed under reduced pressure and the residue diluted with 2N HCl (250 ml) to give a slight precipitate. This was removed by filtration and the filtrate washed with ether (3×150 ml), basified (Na$_2$CO$_3$) and extracted with CH$_2$Cl$_2$ (4×100 ml). The extracts were dried (MgSO$_4$) and the solvent removed under reduced pressure. The residue was dissolved in EtOAc to give a slight precipitate which was removed by filtration. The filtrate was concentrated under reduced pressure and the residue dissolved in xylene (500 ml) to give a slight precipitate which was removed by filtration. The filtrate was concentrated under reduced pressure and the residue dissolved in methanol (500 ml) and treated with decolourising charcoal for 18 hours. The solution was then filtered and the filtrate concentrated under reduced pressure. The residue was purified initially by chromatography on silica using EtOAc as eluent, and finally by h.p.l.c. using 40% EtOAc in CH$_2$Cl$_2$. The purified material was treated with ethereal hydrogen chloride and recrystallised from propan-2-ol to give the title compound as the di-HCl salt (1.8 g) mp 226°–229° C. decomp. Analysis: Found: C, 51.1; H, 4.1; N, 13.05 C$_{14}$H$_{11}$N$_3$S.2HCl requires: C, 51.5; H, 4.0; N, 12.9%

EXAMPLE 2

2,3-Dihydro-2-(2-pyridyl)thiazolo[3,2-a]benzimidazole-1-oxide 2,3-Dihydro-2-(2-pyridyl)thiazolo[3,2-a]benzimidazole. (2 g) was dissolved in ethyl acetate (150 ml) and the solution cooled to −50° C. A solution of m-chloroperoxybenzoic acid (1.7 g) in ethyl acetate (30 ml) was added and the temperature of the mixture allowed to rise to ambient temperature. The mixture was washed with saturated sodium carbonate solution (5 ml) and dried (MgSO$_4$). The solvent was concentrated under reduced pressure keeping the temperature below 30° C. The title compound precipitated out as the ¼ hydrate, (0.9 g). mp 177° C. decomp.

Analysis:
Found: C, 61.6; H, 4.2; N, 15.6.
$C_{14}H_{11}N_3OS.\frac{1}{4}H_2O$ requires C, 61.35; H, 4.2; N, 15.35%.

EXAMPLE 3

2,3-Dihydro-2-phenylthiazolo[3,2-a]benzimidazole (1,2-Dibromoethyl)benzene (21 g) was treated with 2-mercaptobenzimidazole (17 g) in dimethylformamide (100 ml) and the mixture was heated at 100° C. for 36 hours. On cooling, the solid material was removed by filtration and recrystallised from methanol and ethyl acetate to give the title compound as the hydrobromide salt (13.68 g). mp 207°-210° C.

Analysis:
Found: C, 53.8; H, 4.1; N, 8.5.
$C_{15}H_{12}N_2S.HBr$ requires C, 54.1; H, 3.9; N, 8.4%.

EXAMPLE 4

2,3-Dihydro-2-phenylthiazolo[3,2-a]benzimidazole-1-oxide 2,3-Dihydro-2-phenylthiazolo[3,2-a]benzimidazole (4.25 g) was dissolved in ethyl acetate (250 ml) and cooled to −50° C. Solid m-chloroperoxybenzoic acid was added and the mixture allowed to warm to −30° C., at which point saturated sodium carbonate solution (10 ml) was added and allowed to freeze.

On reaching ambient temperature the reaction mixture was filtered and dried (MgSO₄) and the solvent removed by evaporation to give a white residue. This was recrystallised twice from ethyl acetate to give the title compound as the ¼ hydrate (0.75 g) mp 162.5°-163° C.

Analysis:
Found: C, 65.7; H, 4.7; N, 10.0.
$C_{15}H_{12}N_2OS.\frac{1}{4}H_2O$ requires C, 66.0; H, 4.6; N, 10.3%.

EXAMPLE 5

2,3-Dihydro-2-(6-methylpyrid-3-yl)thiazolo[3,2-a]-benzimidazole 3-(1,2-Dibromoethyl)-6-methylpyridine hydrobromide (2.5 g) was added to 2-mercaptobenzimidazole (1.25 g) in dimethylformamide (50 ml). The mixture was stirred at ambient temperature for 4 days and then heated at 100° C. for a further 2 days. The solvent was removed under reduced pressure and the residue diluted with 2N HCl, filtered and extracted with ethyl acetate. The aqueous layer was basified with sodium hydroxide and extracted with ethyl acetate (3×100 ml), dried (MgSO₄) and the solvent removed. The residue was purified by chromatography on Fluorisil using 10% cyclohexane in ethyl acetate as eluent. The solvent was removed and the residue dissolved in 25 ml ether and ethereal HCl added. The solid obtained was recrystallised from methanol/ethyl acetate to give the title compound as the dihydrochloride, hydrate salt (1.3 g) mp greater than 270° C.

Analysis:
Found: C, 49.9; H, 4.45; N, 11.65.
$C_{15}H_{13}N_3S.2HCl.H_2O$ requires C, 50.3; H, 4.8; N, 11.7%.

EXAMPLE 6

6,7-Dichloro-2,3-dihydro-2-(6-methylpyrid-3-yl)thiazolo[3,2-a]benzimidazole

To 5,6-dichloro-2-mercaptobenzimidazole (7.5 g) in dimethylformamide (200 ml) was added 3-(1,2-dibromoethyl)-6-methylpyridine hydrobromide (7.5 g). The mixture was stirred at ambient temperature for 3 days, and then heated at 100° C. for 3 days. The solvent was removed by evaporation and the residue diluted with 2N HCl, filtered through keiselghur and extracted with chloroform (3×125 ml). The aqueous solution was then basified with Na₂CO₃ and extracted with dichloromethane (3×300 ml). The extracts were dried (MgSO₄) and the solvent removed under reduced pressure. The residue was washed with ethyl acetate (5×2 ml), dissolved in hot propan-2-ol and ethereal HCl was added. The solid obtained was recrystallised from methanol/ethyl acetate to give the title compound as the dihydrochloride, ¼ hydrate salt (3.1 g) mp >325° C.

Analysis:
Found: C, 43.9; H, 3.4; N, 10.00
$C_{15}H_{11}Cl_2N_3S.2HCl.\frac{1}{4}H_2O$ requires C, 43.55; H, 3.3; N, 10.2%

EXAMPLE 7

2,3-Dihydro-6-methyl-2-(2-pyridyl)thiazolo[3,2-a]benzimidazole and
2,3-Dihydro-7-methyl-2-(2-pyridyl)thiazolo[3,2-a]benzimidazole 2-(1,2-Dibromoethyl)pyridine hydrobromide (9.5 g) was added to 5-methyl-2-mercaptobenzimidazole (5 g) in dimethylformamide (100 ml) and the mixture stirred at ambient temperature for 3 hours and then heated at 100° C. for 24 hours. The solvent was removed and the residue was dissolved in 2N HCl. The resulting solution was filtered through keiselghur and then extracted with ethyl acetate. The aqueous layer was basified (Na₂CO₃) and extracted with chloroform. The extracts were dried (MgSO₄) and the solvent removed under reduced pressure. The residue was purified by chromatography on fluorisil with 25% v/v chloroform in ethylacetate and then on silica using 10% v/v hexane in ethylacetate. The solvent was removed and the residue dissolved in hot propan-2-ol and ethereal HCl was added. The product obtained was recrystallised from methanol/ethylacetate to give a mixture of the title compounds as the dihydrochloride hemihydrate salts (1.24 g) mp 212°-214° C. decomp.

Analysis:
Found: C, 51.4; H, 4.45; N, 12.0.
$C_{15}H_{13}N_3S.2HCl.\frac{1}{2}H_2O$ requires C, 51.6; H, 4.6; N, 12.0%.

EXAMPLE 8

6,7-Dichloro-2,3-dihydro-2-(2-pyridyl)thiazolo[3,2-a]benzimidazole 2-(1,2-Dibromoethyl)pyridine hydrobromide (10.1 g) was added to 5,6-dichloro-2-mercaptobenzimidazole (7.1 g) in dimethylformamide and the mixture left at ambient temperature for 24 hours, after which it was heated at 100° C. for 3 days. The solvent was removed under reduced pressure and the residue dissolved in 2N HCl and extracted with ethyl acetate. The aqueous layer was basified (Na₂CO₃) and extracted with ethyl acetate. The organic extracts were dried (MgSO₄) and the solvent removed under reduced pressure. The residue was purified by chromatography on fluorisil using 30% v/v chloroform in ethyl acetate and then on fluorisil using ethyl acetate as eluent. The solvent was removed under reduced pressure and the residue washed with a small volume of ethyl acetate. The residue was then dissolved in hot propan-2-ol and ethereal HCl was added. The solid obtained was filtered and dried to give the title compound as the dihydrochloride salt (1.3 g) mp 233°–235° C.

Analysis:
Found: C, 42.5; H, 3.1; N, 10.5.
$C_{14}H_9Cl_2N_3S.2HCl$ requires C, 42.6; H, 2.8; N, 10.6%.

EXAMPLE 9

2,3-Dihydro-6,7-dimethyl-2-(2-pyridyl)thiazolo[3,2-a]benzimidazole 2-(1,2-Dibromoethyl)pyridine hydrobromide (9.7 g) was added to 5,6-dimethyl-2-mercaptobenzimidazole (5.3 g) in methanol (100 ml) and the mixture was heated at reflux for 18 hours, after which time the solvent was removed under reduced pressure. The residue was treated with saturated sodium carbonate solution and extracted into dichloromethane. The extracts were dried (MgSO$_4$) and evaporated and the residue was purified by chromatography on silica using ethyl acetate as eluent. The solvent was removed under reduced pressure and the residue dissolved in hot propan-2-ol and ethereal HCl was added. The product obtained was recrystallised from methanol and ethyl acetate to give the title compound as the dihydrochloride, hemihydrate (0.75 g, 7.35%) mp 222° C. decomp.

Analysis:
Found: C, 53.0; H, 4.8; N, 11.3.
$C_{16}H_{15}N_3S.2HCl.\frac{1}{2}H_2O$ requires C, 52.9; H, 5.0; N, 11.6%.

EXAMPLE 10

2,3-Dihydro-6-methyl-2-(2-pyridyl)thiazolo[3,2-a]benzimidazole-1-oxide and
2,3-Dihydro-7-methyl-2-(2-pyridyl)thiazolo[3,2-a]benzimidazole-1-oxide A mixture of 6- and 7-methyl-2,3-dihydro-2-(2-pyridyl)thiazolo[3,2-a]benzimidazoles (1.57 g) was dissolved in ethyl acetate (120 ml) and cooled to 0° C. m-Chloroperoxybenzoic acid (1.09 g) was added and the mixture stirred for 1 hour. More m-chloroperoxybenzoic acid (0.1 g) was added and the mixture was left a further ½ hour. Saturated sodium carbonate solution was added and the reaction mixture was filtered. The organic layer was dried (MgSO$_4$) and evaporated to low volume. Acetonitrile (0.5 ml) was added and the product crystallised. The solid was isolated by filtration and was washed with acetonitrile and with ether to give a mixture of the quarterhydrates of the title compounds (1 g) mp 153° C.

Analysis:
Found: C, 62.5; H, 4.6; N, 14.3.
$C_{15}H_{13}N_3OS.\frac{1}{4}H_2O$ requires C, 62.6; H, 4.8; N, 14.6%.

EXAMPLE 11

2,3-Dihydro-6-methoxycarbonyl-2-(2-pyridyl)-thiazolo[3,2-a]benzimidazole and
2,3-Dihydro-7-methoxycarbonyl-2-(2-pyridyl)-thiazolo[3,2-a]benzimidazole Methyl 2-mercaptobenzimidazole-5-carboxylate (13.18 g) was suspended in 2-methylpropan-2-ol (180 ml) and potassium tert-butoxide (7.08 g) was added. The mixture was left to stir 1 hour and then 2-(1,2-dibromoethyl)pyridine hydrobromide (21.82 g) was added. Stirring continued for 1 hour at ambient temperature and then 2 hours at reflux.

The mixture was filtered and the solid obtained washed with ether. The filtrate was evaporated to dryness and the residue combined with the solid obtained by filtration and the combined material was dissolved in 2N HCl. The aqueous solution was extracted with ethyl acetate, basified (Na$_2$CO$_3$) and then extracted with dichloromethane. The organic layer was dried (MgSO$_4$) and evaporated to dryness. The residue was purified by chromatography on fluorisil using chloroform as eluent and then on silica using 1:1 v/v methyl acetate and chloroform. The solvent was removed and the residue recrystallised from methyl acetate/cyclohexane to give a mixture of the title compounds (5.30 g) mp 123° C.

Analysis:
Found: C, 61.9; H, 4.4; N, 13.3.
$C_{16}H_{13}N_3O_2S$ requires C, 61.7; H, 4.2; N, 13.5%.

EXAMPLE 12

2,3-Dihydro-6-methoxycarbonyl-7-methyl-2-(2-pyridyl)thiazolo[3,2-a]benzimidazole and
2,3-dihydro-7-methoxycarbonyl-6-methyl-2-(2-pyridyl)thiazolo[3,2-a]benzimidazole 2-Mercapto-5-methoxycarbonyl-6-methylbenzimidazole (2.8 g) was suspended in 2-methyl-2-propanol (50 ml) and potassium tert-butoxide (1.41 g) was added. The reaction mixture was stirred under nitrogen for one hour at 30° C. Then 2-(1,2-dibromoethyl)pyridine hydrobromide (4.36 g) was added all at once and the reaction mixture stirred at 30° C. for 1 hour and then at reflux for 2.5 hours.

The solvent was removed under reduced pressure and the resulting residue treated with 2N HCl (10 ml) and water (100 ml). Insoluble solid was filtered off. The resulting filtrates were washed with ethyl acetate and basified (2N NaOH) and extracted with dichloromethane. The dichloromethane extract was dried (MgSO$_4$) and evaporated to dryness under reduced pressure. The resulting residue was purified by column chromatography, first, on alumina (grade III) using dichloromethane as the eluent and then on silica using CH$_2$Cl$_2$/MeOAc (1:1 v/v) as the eluent. The solvents were removed under reduced pressure and the resulting residue treated with methyl acetate (1 ml), hexane (1 ml) and diethyl ether (1 ml). The resulting solid was removed by filtration, washed with a small amount of ether and dried to give a mixture of the title compounds (0.75 g) mp 104°–106° C.

Analysis:
Found: C, 62.7; H, 4.9; N, 12.6.
$C_{17}H_{15}N_3O_2S$ requires C, 62.75; H, 4.65; N, 12.9%.

EXAMPLE 13

2,3-Dihydro-6,7-dimethyl-2-(2-pyridyl)thiazolo[3,2-a]benzimidazole-1-oxide

In a manner analogous to Example 10 2,3-Dihydro-6,7-dimethyl-2-(2-pyridyl)thiazolo- [3,2-a]benzimidazole (2.63 g) was reacted with m-chloroperoxybenzoic acid (1.45 g) to give the title compound as the ¼ hydrate, mp 177°–8° C. decomp.

Analysis:
Found: C, 64.0; H, 5.1; N, 13.7.
$C_{16}H_{15}N_3OS.\frac{1}{4}H_2O$ requires C, 63.7; H, 5.2; N, 13.9%.

EXAMPLE 14

6-Chloro-2,3-dihydro-2-(2-pyridyl)thiazolo[3,2-a]benzimidazole and
7-Chloro-2,3-dihydro-2-(2-pyridyl)thiazolo[3,2-a]benzimidazole 5-Chloro-2-mercaptobenzimidazole (9.25 g) was added to a solution of sodium (1.15 g) in ethanol (200 ml) and was stirred for 5 minutes. 2-(1,2-Dibromoethyl)pyridine hydrobromide (17.3 g) was added and the mixture was heated at reflux for 1.25 hours. Further sodium ethoxide (1 equiv.) was added and the mixture heated at reflux for 3 hours. The reaction mixture was filtered and the solvent evaporated under reduced pressure. The residue was dissolved in chloroform (200 ml) and was washed with 2% sodium hydroxide solution (200 ml) and brine and then dried ($MgSO_4$). The solvent was removed under reduced pressure and the residue dissolved in ethyl acetate and filtered.

The filtrate was evaporated under reduced pressure and the residue purified by repeated chromatography on silica using ethyl acetate as eluent. The solvent was removed under reduced pressure and the solid obtained was dried under vacuum to give a mixture of the title compounds (1.4 g) mp 89.5°–93° C.

Analysis:
Found: C, 58.8; H, 3.6; N, 14.5.
$C_{14}H_{10}ClN_3S$ requires C, 58.4; H, 3.5; N, 14.6%.

EXAMPLE 15

7-Ethoxy-2,3-dihydro-2-(2-pyridyl)thiazolo[3,2-a]benzimidazole

5-Ethoxy-2-mercaptobenzimidazole (6.03 g) was suspended in 2-methylpropan-2-ol (100 ml) at 50° C. Potassium tert-butoxide (3.48 g) was added and the mixture stirred for 1 hour. The temperature was allowed to fall to 35° C. and 2-(1,2-dibromoethyl)pyridine hydrobromide (10.76 g) was added. The resulting mixture was stirred for 1 hour at 35° C. and then 2 hours at reflux.

The reaction mixture was filtered and the solid washed with ether. The mother liquors were evaporated under reduced pressure and the residue was combined with the solid obtained by filtration. The combined solids were dissolved in 2N HCl and washed with ethyl acetate (4×75 ml), basified ($Na_2CO_3$) and extracted with dichloromethane (3×100 ml). The organic layer was dried ($MgSO_4$) and evaporated under reduced pressure. The residue was purified by chromatography on fluorisil using chloroform as eluent. The solvent was removed under reduced pressure when the residue crystallised to give the title compound (1.2g) mp 164°–166° C.

Analysis:
Found: C, 64.4; H, 5.2; N, 14.3.
$C_{16}H_{15}N_3OS$ requires C, 64.6; H, 5.1; N, 14.1%.

EXAMPLE 16

2,3-Dihydro-7-methoxycarbonyl-6-methyl-2-(2-pyridyl)thiazolo[3,2-a]benzimidazole-1-oxide and
2,3-dihydro-6-methoxycarbonyl-7-methyl-2-(2-pyridyl)thiazolo[3,2-a]benzimidazole-1-oxide In a manner analogous to Example 10 a solution of 2,3-dihydro-6-methoxycarbonyl-7-methyl-2-(2-pyridyl)thiazolo[3,2-a]benzimidazole and 2,3-dihydro-7-methoxycarbonyl-6-methyl-2-(2-pyridyl)-thiazolo[3,2-a]benzimizdazole (0.65g) in dichloromethane (15 ml) was reacted with m-chloroperoxybenzoic acid (0.43 g) to give a mixture of the title compounds (117 mg) 150°–151° C.

Analysis:
Found: C, 59.7; H, 4.7; N, 12.40
$C_{17}H_{15}N_3O_3S$ requires C, 59.8; H, 4.4; N, 12.3%.

EXAMPLE 17

2,3-Dihydro-6-methoxycarbonyl-2-(2-pyridyl)-thiazolo[3,2-a]benzimidazole-1-oxide and
2,3-dihydro-7-methoxycarbonyl2-(2-pyridyl)-thiazolo[3,2-a]benzimidazole-1-oxide In a manner analogous to Example 10 a mixture of 2,3-dihydro-6-[and 7]-methoxycarbonyl-2-(2-pyridyl)thiazolo[3,2-a]benzimidazole (prepared according to Example 12, 1.81 g) was reacted with m-choroperoxybenzoic acid (1.16 g) to give a mixture of the title compounds (500 mg) mp 128°–35° C.

Analysis:
Found: C, 58.5; H, 4.3; N, 12.6.
$C_{16}N_{13}N_3O_3S$ requires C, 58.7; H, 4.0; N, 12.8%.

EXAMPLE 18

6-Chloro-2,3-dihydro-2-(2-pyridyl)thiazolo[3,2-a]benzimidazole-1-oxide and
7-chloro-2,3-dihydro-2-(2pyridyl)-thiazolo[3,2-a]benzimidazole-1-oxide In a manner analogous to Example 10 a mixture of 6- and 7-chloro-2,3-dihydro-2-(2-pyridyl)-thiazolo [3,2-a]benzimidazole (prepared according to Example 13, 2.62 g) was reacted with m-chloroperoxybenzoic acid (1.81 g) to give a mixture of the title compounds (1.9 g) mp 163.5°–4.5° C.

Analysis:
Found: C, 55.6; H, 3.6; N, 14.0.
$C_{14}H_{10}ClN_3OS$ requires C, 55.4; H, 3.3; N, 13.8%.

EXAMPLE 19

Using a procedure analogous to Example 1 involving reaction of compounds of formulae IV and V

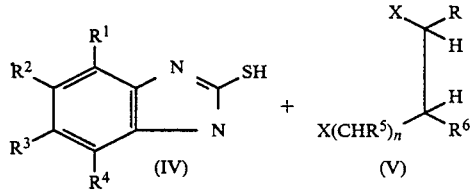

wherein X is Cl or Br, the following compounds of formula I wherein m is 0 are prepared:

| $R^1$ | $R^2$ | $R^3$ | $R^4$ | R | n | $R^6$ | $R^5$ |
|---|---|---|---|---|---|---|---|
| H | H | H | H | 6-carbamoylpyrid-2-yl | 0 | H | H |
| H | H | H | H | 2-pyridyl | 1 | H | H |
| H | H | H | H | 6-cyanopyrid-2-yl | 0 | H | — |
| H | $CO_2Me$ | $CO_2Me$ | H | 2-pyridyl | 0 | H | — |
| H | H | H | H | 4-chloro-2-pyridyl | 0 | H | — |
| H | H | H | H | 2-thienyl | 0 | H | — |
| H | $CF_3$ | H | H | 4-pyridyl | 0 | H | — |
| H | H | H | H | 2-pyrimidinyl | 0 | H | — |
| H | H | H | H | 3-chlorophenyl | 0 | H | — |
| H | H | H | H | 4-methylphenyl | 0 | H | — |
| H | H | H | H | 4-methoxyphenyl | 0 | H | — |
| H | H | H | H | 4-methoxycarbonyl-phenyl | 0 | H | — |
| H | H | H | H | 2-acetoxyphenyl | 0 | H | — | which compounds are all converted to their S-oxides by a method analogous to Example 2.

EXAMPLE 20

2,3-Dihydro-5-methyl-2-(2-pyridyl)thiazolo[3,2-a]benzimidazole

4-Methyl-2-mercaptobenzimidazole (13.32 g) was suspended in 2-methylpropan-2-ol (150 ml) and potassium tertbutoxide (9.04 g) added. The mixture was stirred for 2 hours and 2-(1,2-dibromoethyl)pyridine hydrobromide (27.68 g) added. The mixture was stirred at ambient temperature for 1 hour and then at reflux for 2 hours. The reaction mixture was filtered and the solid washed with ether. The filtrate was evaporated to dryness under reduced pressure and the residue combined with the first solid obtained. The combined material was dissolved in 2N HCl (100 ml). The aqueous solution was extracted with ethyl acetate, basified ($Na_2CO_3$) and extracted with dichloromethane. The organic layer was dried ($MgSO_4$) and the solvent removed under reduced pressure. The residue was purified on Florisil using chloroform as eluent and on silica using ethyl acetate as eluent to give the title compound (1.55 g) mp 128°–130° C.

Analysis:
Found: C, 67.1; H, 5.0; N, 16.1.
$C_{15}H_{13}N_3S$ requires: C, 67.4; H, 4.9; N, 15.7%.

EXAMPLE 21

2,3-Dihydro-8-methyl-2-(2-pyridyl)thiazolo[3,2-a]benzimidazole

Also isolated from the purification step in Example 20 was the title compound (1.5 g) m.p. 96° C.
Analysis:
Found: C, 67.05; H, 4.9; N, 15.7.
$C_{15}H_{13}N_3S$ requires: C, 67.4; H, 4.9; N, 15.7%.

EXAMPLE 22

2,3-Dihydro-5-methyl-2-(2-pyridyl)thiazolo[3,2-a]benzimidazole-1-oxide

In a similar manner to Example 4 2,3-dihydro-5-methyl-2-(2-pyridyl)thiazolo[3,2-a]-benzimidazole (1.07 g) was reacted with m-chloroperoxybenzoic acid to give the title compound (0.74 g, 70%) mp 148.5° C.
Analysis:
Found: C, 63.4; H, 4.6; N, 14.7.
$C_{15}H_{13}N_3OS$ requires: C, 63.6; H, 4.6; N, 14.8%.

EXAMPLE 23

2,3-Dihydro-8-methyl-2-(2-pyridyl)thiazolo[3,2-a]benzimidazole-1-oxide

In a manner analogous to Example 4 2,3-dihydro-8-methyl-2-(2-pyridyl)thiazolo[3,2-a]-benzimidazole (1.04 g) was reacted with m-chloroperoxybenzoic acid (0.85 g) to give the title compound (0.83 g. 80%) mp 182° C decomp.
Analysis:
Found:C,63.2; H, 4.6; N, 15.0.
$C_{15}H_{13}N_3OS$ requires C, 63.6; H, 4.6; N, 14.8%.

EXAMPLE 24

7-Ethoxy-2,3-dihydro-2-(2-pyridyl)thiazolo[3,2-a]benzimidazole-1-oxide

In a manner analogous to Example 4 7-ethoxy-2,3-dihydro-2-(2-pyridyl)thiazolo[3,2-a]-benzimidazole (1.65 g) was reacted with m-chloroperoxy benzoic acid (1.25) to give the title compound (0.56 g, mp 145°–147° C.

Analysis:
Found: C, 61.3; H, 4.8; N, 13.7.
$C_{16}H_{15}N_3O_2S$ requires: C, 61.3; H, 4.8; N, 13.4%.

EXAMPLE 25

2,3-Dihydro-2-(2-(5-ethylpyridyl))thiazolo[3,2-a]benzimidazole

5-Ethyl-2-vinylpyridine (12.0 g) (J. Amer. Chem. Soc., 68 1368 (1946)) was dissolved in dichloromethane (40 ml) and cooled to ice temperature with stirring. Then bromine (15.8 g) dissolved in dichloromethane (30 ml) was added dropwise over a period of 5 minutes and the reaction mixture stirred for further 10 minutes at ice temperature.

Anhydrous HBr gas was bubbled through the reaction solution in excess amount and solvent was removed under reduced pressure. The resulting residue was treated with propan-2-ol (10 ml) and the resulting yellow solid filtered, washed with ether and dried to yield 2-(1,2-dibromoethyl)-5-ethylpyridine hydrobromide (29.0 g) (86%).

2-Mercaptobenzimidazole (10.84 g) was suspended in 2-methylpropan-2-ol (170 ml) and potassium tert-butoxide (8.1 g) in 2-methylpropan-2-ol (70 ml) added and the reaction mixture stirred under nitrogen for 1 hour at 50° C. The reaction was then cooled to room temperature and 2-(1,2-dibromoethyl)-5-ethylpyridine hydrobromide (27.0 g) was added at once and the reaction mixture stirred at room temperature for 2 hours and then refluxed for 2 hours. Further potassium tert-butoxide (8.1 g) was added and the reaction mixture refluxed for 2.5 hours.

The solvent was removed under reduced pressure and the resulting residue treated with 2N HCl (200 ml) and water (100 ml) and the insoluble solid filtered off.

The resulting filtrate was washed with ethyl acetate and basified (2N NaOH) and extracted with dichloromethane. The dichloromethane extracts were dried ($MgSO_4$) and evaporated to dryness under reduced pressure.

The resulting residue was purified by column chromatography, first, on alumina (grade III) using dichloromethane as the eluent and then on silica using EtOAc/hexane (85.15 v/v) as the eluent. The solvents were removed under reduced pressure from the fractions having Rf value about 0.29 and the resulting residue treated with methyl acetate (2 ml). The resulting white solid was removed by filtration, washed with a small amount of hexane and dried to give the title compound (7.4 g). m.p. 101°–102° C.
Analysis:
Found: C, 68.6; H, 5.4; N, 14.7.
$C_{16}H_{15}N_3S$ requires C, 68.3; H, 5.4; N, 14.9%.

EXAMPLE 26

2,3-Dihydro-2-(2-(5-ethylpyridyl))thiazolo[3,2-a]benzimidazole-1-oxide

In a manner analogous to Example 4 2,3-dihydro-2-(2-(5-ethylpyridyl)) thiazolo[3,2-a]benzimidazole was reacted with m-chloroperoxybenzoic acid (1.2 g) to give the title compound (0.91 g) m.p. 154°–155° C.
Analysis:
Found: C, 64.5; H, 5.3; N, 13.7.
$C_{16}H_{15}N_3OS$ requires C, 64.6; H, 5.1; N, 14.1%.

EXAMPLE 27

6-Cyano-2,3-dihydro-2-(2-pyridyl)thiazolo[3,2-a]benzimidazole and
7-Cyano-2,3-dihydro-2-(2-pyridyl)thiazolo[3,2-a]benzimidazole In a manner analogous to Example 12, 5-cyano-2-mercaptobenzimidazole (10.46 g) was reacted with 2-(1,2-dibromoethyl)pyridine hydrobromide (20.76 g) in the presence of potassium tert-butoxide (15.46 g) to give the title compound (0.24 g), m.p. 158°–160° C.
Analysis:
Found: C, 64.4; H, 3.6; N, 19.85; $C_{15}H_{10}N_4S$.
requires C, 64.7; H, 3.6; N, 20.1%.

EXAMPLE 28

2,3-Dihydro-2-[2-(4-methoxypyridyl)]thiazolo[3,2-a]benzimidazole (a) 2-Bromoacetyl-4-methoxypyridine (11.5 g, 0.05) and 2-chlorobenzimidazole (7.5 g, 0.05 mole) were dissolved in dimethylformamide (75 ml) and cooled to 2° C. $K_2CO_3$ (12 g, 0.08 mole) was added and the temperature rose to 9° C. as the suspension was stirred for ¼ hour. The mixture was added to $H_2O$ (200 ml) giving a solid which was removed by filtration. The mother liquors were extracted with ethyl acetate and the solid was dissolved in the extracts. The organic solution was washed (brine) and dried (MgSO4) and purified by passage down a silica column and evaporated to dryness to give a sticky solid. Trituration with propan-2-ol/di-isopropyl ether gave 2-chloro-1-[2-[4-methoxypyridyl])-2-oxoethyl]-benzimidazole (7.2 g).

(b) A mixture of the product of step (a) (7.2 g) and thiourea (2.4 g) in ethanol (50 ml) was stirred at ambient temperature for ¼ hour and heated at 60° C. for 2 hours. The solution was filtered and evaporated and the residue was dissolved in water and treated to excess with NH4OH to give a solid which was purified by chromatography on silica with ethyl acetate to give 2-mercapto-1-(2-(2-(4-methoxypyridyl))-2-oxoethyl)benzimidazole (2 g.).

(c) The product of step (b) was dissolved in 0.1N NaOH (70 ml) and ethanol (30 ml) and the solution was treated with NaBH4 (0.3 g.). After stirring at ambient temperature for 1 hour, the resulting solution was treated with charcoal, filtered and evaporated to low volume. The residue was acidified to pH5 with acetic acid and the aqueous solution decanted. The residue was crystallised from propan-2-ol to give 1-[2-hydroxy-2-(2-(4-methoxypyridyl))ethyl]-2-mercaptobenzimidazole (1.1 g.).

(d) The product of step (c) (0.5 g.) was dissolved in polyphosphoric acid (1.7 g) and was heated at 120° C. for 1½ hour with stirring. Further 1-[2-hydroxy-2-(2-(4-methoxypyridyl)ethyl]-2-mercaptobenzimidazole (0.5 g.) was added and the heating continued 1½ hours. The solution was basified with $Na_2CO_3$ solution to give a solid which was extracted with ethyl acetate. The extracts were dried (MgSO4) and evaporated and the residue triturated with di-isopropyl ether to give the title compound (0.85 g.) mp 107°–8° C.
Analysis:
Found: C, 63.5; H, 4.8; N, 14.5.
$C_{15}H_{13}N_3OS$ requires C, 63.6; H, 4.6; N, 14.8%.

EXAMPLE 29

2,3-Dihydro-2-[2-(6-methylpyridyl)]thiazolo[3,2-a]benzimidazole

In a manner analogous to Example 28 steps a)→d) 2-bromoacetyl-6-methylpyridine (11.4 g) was reacted with 2-chlorobenzimidazole (8.2 g) to give 1-[2-(6-methylpyrid-2-yl)-2-oxoethyl]-2-chlorobenzimidazole (8.4 g). This wasreacted with thiourea, then NH4OH to give 1-[2-(6methylpyrid-2-yl)-2-oxoethyl]-2-mercaptobenzimidazole (6.9 g); which compound was reduced with NaBH4 to give 1-[2-hydroxy-2-(6-methylpyrid-2-yl]-2-mercaptobenzimidazole (5.0 g.) Treatment of this with polyphosphoric acid gave the title compound (2.1 g.) m.p. 79°–81° C.
Analysis:
Found: C, 67.0; H, 4.8; N, 15.6%. $C_{15}H_{13}N_3S$.
requires: C, 67.4; H, 4.9; N, 15.7%.

EXAMPLE 30

2,3-Dihydro-2-[2-(6-methylpyridyl)]thiazolo[3,2-a]-benzimidazole-1-oxide

In a manner analogous to Example 4 2,3-dihydro-2-[2-(6-methylpyridyl)]thiazolo[3,2-a]benzimidazole (1.0 g) was reacted with m-chloroperoxybenzoic acid (0.71 g.) to give the title compound as the quarterhydrate, 0.9 g, m.p. 175°–177° C.
Analysis:
Found: C, 62.2; H, 4.4; 14.4%. $C_{15}H_{13}N_3OS \cdot \tfrac{1}{4}H_2O$.
Requires: C, 62.6; H, 4.7; N, 14.6%.

EXAMPLE 31

2,3-Dihydro-2-(2-pyridyl)naphth[2',3':4,5]imidazo[2,1-b]thiazole

In a manner analogous to Example 28 steps a)→d) 2-chloro-1H-naphtho[2,3-d]imidazole (7.5 g) was reacted with 2-bromoacetylpyridine (8.7 g) to give 2-chloro-1-(2-oxo-2-(2-pyridyl)ethyl)naphtho[2,3-d]imidazole (9 g). This was reacted with thiourea (5.5 g) then NH4OH solution (100 ml) to give 2-mercapto-1-(2-oxo-2-(2-pyridyl)ethyl)naphtho[2,3-d]imidazole which compound was reduced with NaBH4 to give 2-mercapto-1-(2-hydroxy-2-(2-pyridyl)ethyl)naphtho[2,3-a]imidazole (1.3 g). Treatment of this with polyphosphoric acid (23 g) gave the title compound (0.75 g.) mp 197.5°–198.5° C.
Analysis:
Found: C, 71.2; H, 4.25; N, 13.5. $C_{18}H_{13}N_3S$ requires: C, 71.3; H, 4.3; N, 13.85%).

EXAMPLE 32

2,3-Dihydro-2-[2-(6-phenylpyridyl)]thiazolo[3,2-a]benzimidazole

In a similar manner to Example 28 steps a)→d) 2-bromoacetyl-6-phenyl pyridine (14.1 g,) is converted to the title compound via the following intermediates: 1-[2-(6-phenylpyrid-2-yl)-2-oxoethyl]-2-chlorobenzimidazole, 1-[2-(6-phenylpyrid-2-yl)-2-oxoethyl]-2-mercaptobenzimidazole and 1-[2-hydroxy-2-(6-phenylpyrid-2-yl)ethyl]-2-mercaptobenzimidazole, m.p. of the title compound=145°-147° C.

Analysis:
Found: C, 73.25; H, 4.9; N, 13.1%.
$C_{20}H_{15}N_3S$ requires C, 72.9; H, 4.6; N, 12.75%.

EXAMPLE 33

(R*R*)-2,3-dihydro-2-(4-methoxypyrid-2-yl)thiazolo[3,2-a]benzimidazole-1-oxide and its (R*,S*) isomer A solution of 2,3-dihydro-2-[2-(4-methoxypyridyl)]thiazolo[3,2-a]benzimidazole (0.6 g) in $CH_2Cl_2$ (30 ml) was cooled to 0°. Purified m-chloroperoxybenzoic acid (0.4 g) was added and the mixture was stirred 1½hr. Further m-chloroperoxybenzoic acid (0.05 g) was added and the mixture was stirred 1 hour and washed ($NaCO_3$ solution and brine), dried ($MgSO_4$) and evaporated. The residue was purified by chromatography on silica with EtOH/EtOAc as eluent followed by recrystallisation from acetonitrile to give as a first product the R*R* isomer of the title compound (105 mg) 193°-5° C.

Analysis:
Found: C, 60.5; H, 4.5; N, 14.1.
$C_{15}H_{13}N_3O_2S$ requires: C, 60.2; N, 4.4; N, 14.0%.

A further component of lower $R_f$ was isolated and recrystallised from acetonitrile to give the corresponding R*S* isomer of the title compound (90% pure) (115 mg) mp 172°-7° C.

EXAMPLE 34

2,3-Dihydro-2-(2-pyridyl)thiazino[3,2-a]benzimidazole (a) 3-(2-Benzimidazolylthio)-3-(2-pyridyl)propionic acid (3.7 g) was suspended in dichloromethane (100 ml) and was cooled to 0° C. N,N'-Dicyclohexylcarbodiimide (2.55 g) was added and the mixture was left to stir until t.l.c. showed no starting material. The solvent was removed under reduced pressure and the residue suspended in acetone and filtered. The solvent was removed under reduced pressure and the residue was dissolved in chloroform. The organic solution was washed with dilute sodium hydrogen carbonate solution then water and was dried ($MgSO_4$). The residue was purified on silica using chloroform as eluent to give 2,3 dihydro-2-(2-pyridyl)-[1,3]-thiazino[3,2-a]benzimidazol-4-one ¼ hydrate (1.8 g,) mp 165.5°-167.5° C. decomp.

Analysis:
Found: C, 63.0; H, 4.2; N, 14.7.
$C_{15}H_{11}N_3OS.\frac{1}{4}H_2O$ requires: C,63.0; H, 4.1; N, 14.7%.

(b) The product of step (a) is reduced using diborane to give the title compound.

EXAMPLE 35

2-(4-Ethylthio-3-methylpyrid-2-yl)-2,3-dihydrothiazolo[3,2-a]benzimidazole (a) 2-Chlorobenzimidazole is reacted with 2-bromoacetyl-4-ethylthio-3-methylpyridine in the presence of $K_2CO_3$ to give 2-chloro-1-[2-[4-ethylthio-3-methylpyridyl])-2-oxoethyl]benzimidazole. This is reacted with thiourea and treated with $NH_4OH$ to give 2-mercapto-1-(2-(2-(4-ethylthio-3-methylpyridyl))-2-oxoethyl)benzimidazole. Reduction of this product using $NaBH_4$ gives 1-[2-hydroxy-2-(4-ethylthio-3-methylpyrid-2-yl)ethyl]-2-mercaptobenzimidazole.

(b) 1-[2-Hydroxy-2-(4-ethylthio-3-methylpyrid-2-yl)ethyl]-2-mercaptobenzimidazole (0.01 mole) is dissolved in polyphosphoric acid (10 g) and the mixture heated at 100° C. for 2 hours with stirring. The mixture is then neutralised with sodium hydroxide solution and the product extracted with chloroform. Purification by column chromatography on silica gives the title compound.

EXAMPLE 36

2-(4-Ethylthio-3-methylpyrid-2-yl)-2,3-dihydrothiazolo[3,2-a]-benzimidazole-1-oxide A solution of 2-(4-ethylthio-3-methylpyrid-2-yl)-2,3-dihydrothiazolo[3,2-a]benzimidazole (0.01 mole) is dissolved in $CH_2Cl_2$ solution (100 ml) at 0° C. and treated with m-chloroperoxybenzoic acid (0.01 mole) for 0.5 hours. The solution is then washed with sodium carbonate solution and dried ($MgSO_4$). Purification by chromatography on silica gives the title compound.

EXAMPLE 37

In a manner analogous to Example 35 the following compounds of formula (IA) are prepared according to the reaction scheme:

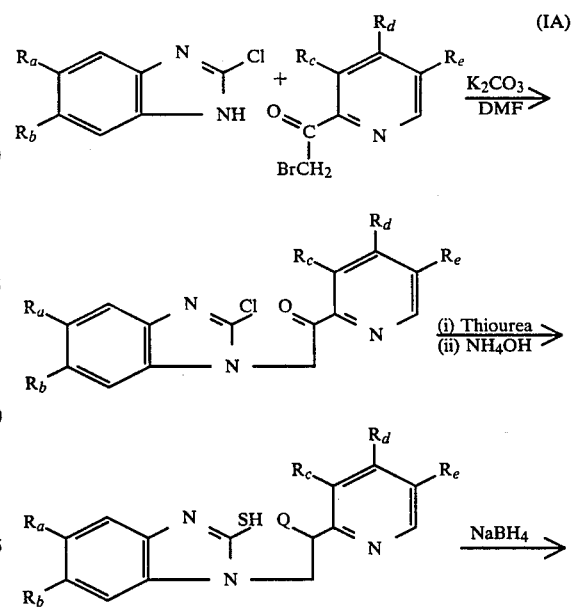

-continued

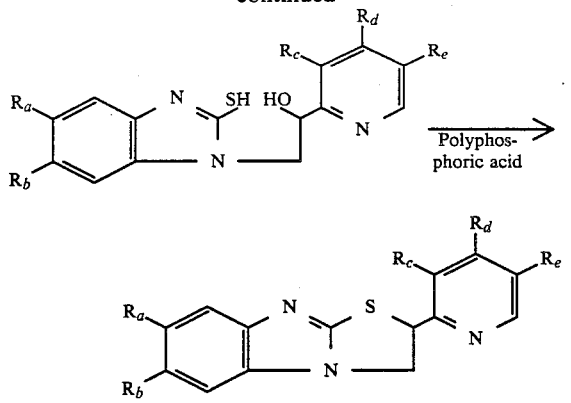

| $R_a$ | $R_b$ | $R_c$ | $R_d$ | $R_e$ |
|---|---|---|---|---|
| H | H | MeO | SEt | H |
| H | H | Me | SMe | H |
| H | H | Me | S$^n$Pr | H |
| OMe | H | Me | SEt | H |
| H | OMe | Me | SEt | H |
| H | H | Et | OPh | H |
| H | H | H | OCH$_2$Ph | H |
| H | H | Et | 4-morpholinyl | H |
| H | H | Et | 1-piperidinyl | H |
| CF$_3$ | H | Me | SEt | H |
| H | H | Me | SEt | Me |
| H | H | H | SPh | Me |
| H | H | Me | SCH=CH$_2$ | H |
| H | H | Me | SCH=CHCH$_3$ | H |
| H | H | Me | SC$_6$H$_{12}$ | H |
| H | H | H | SEt | OMe | which compounds are converted to the sulphoxides in a procedure analogous to Example 36.

I claim:

1. A method of treating ulcers or hypersecretion in a mammal which method comprises administering to said mammal in need of such treatment an effective amount of a compound of formula:

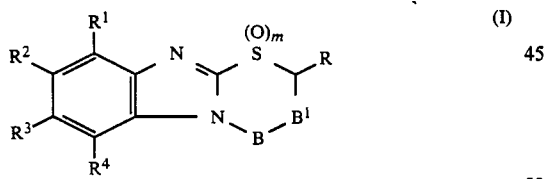

or a pharmaceutically acceptable salt thereof, wherein —B—B$^1$— represents a chain of formula $$-(CHR^5)_n-CHR^6- \qquad (Ia)$$

R represents phenyl, naphthyl or an heteroaryl radical selected from the group pyridyl, thienyl, furyl, thiazolyl, quinolyl, isoquinolyl and indolyl each optionally substituted by not more than three substituents the same or different selected from lower alkylthio, lower alkyl, lower alkoxy, halogen, alkanyloxy of 2 to 7 carbon atoms, lower alkoxycarbonyl, halolower alkyl, hydroxy, cyano, amino, mono- or diloweralkyl amino, lower alkanoylamino, carboxy, carboxylower alkyl, hydroxylower alkyl, carbamoyl, carbamoyloxy, lower alkyl- or phenyl- carbonyl, (loweralkoxy) lower alkoxy, [1-piperidinyl, 4-morpholinyl, 4-loweralkylpiperazinyl, 1-pyrrolidinyl,]OR$^8$, SR$^8$, phenyl and phenyl substituted by one or more substituents as hereinbefore defined excepting phenyl; (where R$^8$ is C$_2$-C$_6$ alkenyl, C$_3$-C$_{10}$ cycloalkyl, phenyl, phenylloweralkyl or phenyl or phenylloweralkyl each carrying from 1 to 3 substituents on the phenyl selected from lower alkyl, halogen, nitro, haloloweralkyl, hydroxy and lower alkoxy); R$^1$, R$^2$, R$^3$ and R$^4$ independently represent hydrogen, or a substituent as mentioned above in connection with the group R, or any adjacent pair of R$^1$, R$^2$, R$^3$ and R$^4$ together with the carbon atoms to which they are attached complete a six membered fully unsaturated carbocyclic ring, said ring being optionally substituted by a substituent as defined above in connection with the group R;

R$^5$ and R$^6$ independently represent hydrogen or lower alkyl; n and m independently represent 0 or 1; the term 'lower' means a group having 1 to 6 carbon atoms.

2. A pharmaceutical composition for treating ulcers or hypersecretion comprising a therapeutically effective amount of a compound of formula

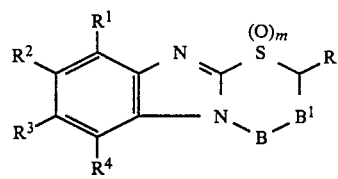

or a pharmaceutically acceptable salt thereof wherein —B—B$^1$— represents a chain of formula $$-(CHR^5)_n-CHR^6- \qquad (Ia)$$

R represents phenyl, naphthyl or an heteroaryl radical selected from the group pyridyl, thienyl, furyl, thiazolyl, quinolyl, isoquinolyl and indolyl each optionally substituted by not more than three substituents the same or different selected from lower alkylthio, lower alkyl, lower alkoxy, halogen, alkanoyloxy of 2 to 7 carbon atoms, lower alkoxy carbonyl, halolower alkyl, hydroxy, cyano, amino, mono- or di-loweralkyl amino, lower alkanoylamino, carboxy, carboxyloweralkyl, hydroxylower alkyl, carbamoyl, carbamoyloxy, lower alkyl- or phenyl- carbonyl, (loweralkoxy) lower alkoxy, [1-piperidinyl, 4-morpholinyl, 4-loweralkylpiperazinyl, 1-pyrrolidinyl,] OR$^8$, SR$^8$, phenyl and phenyl substituted by one or more substituents as hereinbefore defined excepting phenyl; (where R$^8$ is C$_2$-C$_6$ alkenyl, C$_3$-C$_{10}$ cycloalkyl, phenyl, phenylloweralkyl or phenyl or phenylloweralkyl each carrying from 1 to 3 substituents on the phenyl selected from lower alkyl, halogen, nitro, haloloweralkyl, hydroxy and lower alkoxy); R$^1$, R$^2$, R$^3$ and R$^4$ independently represent hydrogen or a substituent as mentioned above in connection with the group R, or any adjacent pair of R$^1$, R$^2$, R$^3$ and R$^4$ together with the carbon atoms to which they are attached complete a six membered fully unsaturated carbocyclic ring, said ring being optionally substituted by a substituent as defined above in connection with the group R;

$R^5$ and $R^6$ independently represent hydrogen or lower alkyl; n and m independently represent 0 or 1; the term 'lower' means a group having 1 to 6 carbon atoms, providing that when n is 1 and m is 0 then R is heteroaryl or heteroaryl optionally substituted as defined hereinbefore, and a pharmaceutically acceptable carrier.

3. A compound of formula

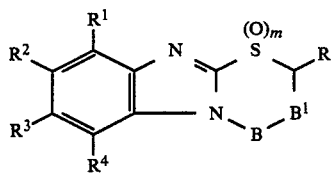

or a pharmaceutically acceptable salt thereof wherein —B—B¹— represents a chain of formula

R represents phenyl, naphthyl or an heteroaryl radical selected from the group pyridyl, thienyl, furyl, thiazolyl, quinolyl, isoquinolyl and indolyl each optionally substituted by not more than three substituents the same or different selected from lower alkylthio, lower alkyl, lower alkoxy, halogen, alkanoyloxy of 2 to 7 carbon atoms, lower alkoxycarbonyl, halolower alkyl, hydroxy, cyano, amino, mono- or diloweralkyl amino, lower alkanoylamino, carboxy, carboxyloweralkyl, hydroxylower alkyl, carbamoyl, carbamoyloxy, lower alkyl- or phenyl- carbonyl, (loweralkoxy)-lower alkoxy, [1-piperidinyl, 4-morpholinyl, 4-loweralkylpiperazinyl, 1-pyrrolidinyl,]$OR^8$, $SR^8$, phenyl and phenyl substituted by one or more substituents as hereinbefore defined excepting phenyl; (where $R^8$ is $C_2$-$C_6$ alkenyl, $C_3$-$C_{10}$ cycloalkyl, phenyl, phenylloweralkyl or phenyl or phenylloweralkyl each carrying from 1 to 3 substituents on the phenyl selected from lower alkyl, halogen, nitro, haloloweralkyl, hydroxy and lower alkoxy), $R^1$, $R^2$, $R^3$ and $R^4$ independently represent hydrogen, or a substituent as mentioned above in connection with the group R, or any adjacent pair of $R^1$, $R^2$, $R^3$ and $R^4$ together with the carbon atoms to which they are attached complete a six membered fully unsaturated carbocyclic ring, said ring being optionally substituted by a substituent as defined above in connection with the group R;

$R^5$ and $R^6$ independently represent hydrogen or lower alkyl; n and m independently represent 0 or 1; the term 'lower' means a group having 1 to 6 carbon atoms with the provisos
(i) that when n is 1 and m is 0 then R is heteroaryl or heteroaryl optionally substituted as defined hereinbefore, and (ii) when n is 0 and $R^1$ and $R^2$ together with the carbon atoms to which they are attached represent a 6-membered unsaturated carbocyclic ring and R is phenyl or p-nitrophenyl, then m is 1.

4. A compound as claimed in claim 3 wherein n is 0.

5. A compound as claimed in claim 3 wherein R represents a phenyl, naphthyl, pyridyl, thienyl, furyl, thiazolyl, quinolyl, isoquinolyl or indolyl group each optionally substituted as defined in claim 3.

6. A compound as claimed in claim 3 wherein R represents phenyl, pyrid-2-yl or pyrid-3-yl each optionally substituted by one to three groups independently selected from lower alkyl, lower alkoxy, halogen, phenyl, halophenyl, lower alkylphenyl, lower alkoxyphenyl and lower alkylthio.

7. A compound as claimed in claim 3 wherein $R^2$ and $R^3$ are selected from hydrogen, lower alkyl, alkoxycarbonyl of 2 to 7 carbon atoms, halogen, cyano or lower alkoxy.

8. A compound as claimed in claim 3 which is 2,3-dihydro-2-(2-pyridyl)thiazolo[3,2-a]benzimidazole-1-oxide or a pharmaceutically acceptable salt thereof.

9. A compound as claimed inb claim 3 which is 6,7-dichloro-2,3-dihydro-2-(6-methylpyrid-3-yl)thiazolo[3,2-a]benzimidazole or a pharmaceutically acceptable salt thereof.

10. A compound as claimed in claim 3 which is 2,3-dihydro-6,7-dimethyl-2-(2-pyridyl)-thiazolo[3,2-a]benzimidazole-1-oxide or a pharmaceutically acceptable salt thereof.

11. A compound as claimed in claim 3 which is 6-chloro-2,3-dihydro-2-(2-pyridyl)thiazolo[3,2-a]benzimidazole-1-oxide or a pharmaceutically acceptable salt thereof.

12. A compound as claimed in claim 3 which is 7-chloro-2,3-dihydro-2-(2-pyridyl)thiazolo[3,2-a]benzimidazole-1-oxide or a pharmaceutically acceptable salt thereof.

13. A compound as claimed in claim 3 which is 6,7-dichloro-2,3-dihydro-2-(2-pyridyl)thiazolo[3,2-a]benzimidazole or a pharmaceutically acceptable salt thereof.

14. A compound as claimed in claim 3 which is 2,3-dihydro-6-methyl-2-(2-pyridyl)thiazolo[3,2-a]benzimidazole-1-oxide or a pharmaceutically acceptable salt thereof.

15. A compound as claimed in claim 3 which is 2,3-dihydro-7methyl-2-(2-pyridyl)thiazolo[3,2-a]-benzimidazole-1-oxide or a pharaceutically acceptable salt thereof.

16. A compound as claimed in claim 3 which is 2,3-dihydro-7-methoxycarbonyl-6-methyl-2-(2-pyridyl)-thiazolo[3,2-a]benzimidazole-1-oxide or a pharmaceutically acceptable salt thereof.

17. A compound as claimed in claim 3 which is 2,3-dihydro-6-methoxycarbonyl-7-methyl-2-(2-pyridyl)-thiazolo[3,2-a]benzimidazole-1-oxide or a pharmaceutically acceptable salt thereof.

18. A compound as claimed in claim 3 which is 2,3-dihydro-6-methoxycarbonyl-2-(2-pyridyl)thiazolo[3,2-a]-benzimidazole-1-oxide or a pharmaceutically acceptable salt thereof.

19. A compound as claimed in claim 3 which is 2,3-dihydro-7-methoxycarbonyl-2-(2-pyridyl)thiazolo[3,2-a]-benzimidazole-1-oxide or a pharmaceutically acceptable salt thereof.

20. A compound as claimed in claim 3 which is 2,3-dihydro-2-[2-(6-phenylpyridyl)]thiazolo[3,2-a]benzimidazole; or a pharmaceutically acceptable salt thereof.

21. A compound as claimed in claim 3 which is racemic (R*,R*)-2,3-dihydro-2-(4-methoxypyrid-2-yl)thiazolo[3,2-a]benzimidazole-1-oxide or a pharmaceutically acceptable salt thereof.

22. A compound as claimed in claim 3, which is 2,3-dihydro-2(2-pyridyl)thiazolo[3,2-a]benzimidazole.

* * * * *